(12) United States Patent
Parker et al.

(10) Patent No.: US 6,239,436 B1
(45) Date of Patent: May 29, 2001

(54) METHOD AND SYSTEM FOR INSPECTING A LOW GLOSS SURFACE OF AN OBJECT AT A VISION STATION

(75) Inventors: Jeffrey B Parker, Houghton; Myron Czubko, Ann Arbor; Neil Haven, Stockbridge, all of MI (US)

(73) Assignee: Perceptron, Inc., Ann Arbor, MI (US)

( * ) Notice: Subject to any disclaimer, the term of this patent is extended or adjusted under 35 U.S.C. 154(b) by 0 days.

(21) Appl. No.: 09/171,504

(22) PCT Filed: Apr. 9, 1997

(86) PCT No.: PCT/US97/05754

§ 371 Date: Dec. 24, 1998

§ 102(e) Date: Dec. 24, 1998

(87) PCT Pub. No.: WO97/40367

PCT Pub. Date: Oct. 30, 1997

Related U.S. Application Data (60) Provisional application No. 60/015,915, filed on Apr. 22, 1996, provisional application No. 60/017,335, filed on Apr. 26, 1996, and provisional application No. 60/028,309, filed on Sep. 6, 1996.

(51) Int. Cl.[7] .................................................. G01N 21/88
(52) U.S. Cl. .................................. 250/341.8; 250/339.11
(58) Field of Search ................................ 250/341.8, 345, 250/339.05, 339.06, 339.11, 572; 356/32, 376, 371, 446; 348/128; 209/581

(56) References Cited

U.S. PATENT DOCUMENTS

| | | |
|---|---|---|
| 4,629,319 | 12/1986 | Clarke et al. . |
| 4,686,374 | 8/1987 | Liptay-Wagner et al. . |
| 4,792,232 | 12/1988 | Jobe et al. . |
| 5,038,038 | 8/1991 | Weniger et al. . |
| 5,041,726 | 8/1991 | Chang et al. . |
| 5,237,404 | 8/1993 | Tanaka et al. . |
| 5,436,726 | 7/1995 | Ventura et al. . |
| 5,726,705 | 3/1998 | Imanishi et al. . |
| 5,734,742 | 3/1998 | Asaeda et al. . |

OTHER PUBLICATIONS

Optical Digital Detection of Dents and Scratches on Specular Metal Surfaces, Applied Optics, Aug. 15, 1982. vol. 21, No. 18, p. 2875.

*Primary Examiner*—Georgia Epps
*Assistant Examiner*—Richard Hanig
(74) *Attorney, Agent, or Firm*—Brooks & Kushman P.C.

(57) ABSTRACT

A method and system are provided for inspecting a low gloss surface (12) of an object (14) at a vision station utilizing a regular, extended pattern of infrared radiation. The system includes an infrared radiation source (10) and an infrared image converter and/or infrared cameras (16) to automatically locate a surface defect in the object. A signal processor processes a first set of electrical signals from the infrared cameras to obtain a second set of electrical signals which represent pattern distortions in the reflected infrared radiation signal caused by the surface defect in order to locate the surface defect in the object. The second set of electrical signals may be processed to classify the surface defect in the object as being an "in-dent" or an "out-dent".

26 Claims, 8 Drawing Sheets

METHOD AND SYSTEM FOR INSPECTING
A LOW GLOSS SURFACE OF AN OBJECT
AT A VISION STATION

This application claims the benefit of the following three provisional patent applications: Serial No. 69/015,915 filed Apr. 22, 1996; Serial No. 60/017,335 filed Apr. 26, 1996; and Serial No. 60/028,309 filed Sep. 6, 1996.

TECHNICAL FIELD

This invention relates to methods and systems for inspecting a low gloss surface of an object at a vision station and, in particular, to methods and systems for inspecting a low gloss surface of an object at a vision station utilizing radiation having a wavelength longer than the wavelength of visible light, but shorter than the dimension of a surface defect to be detected.

BACKGROUND ART

Figure 1:
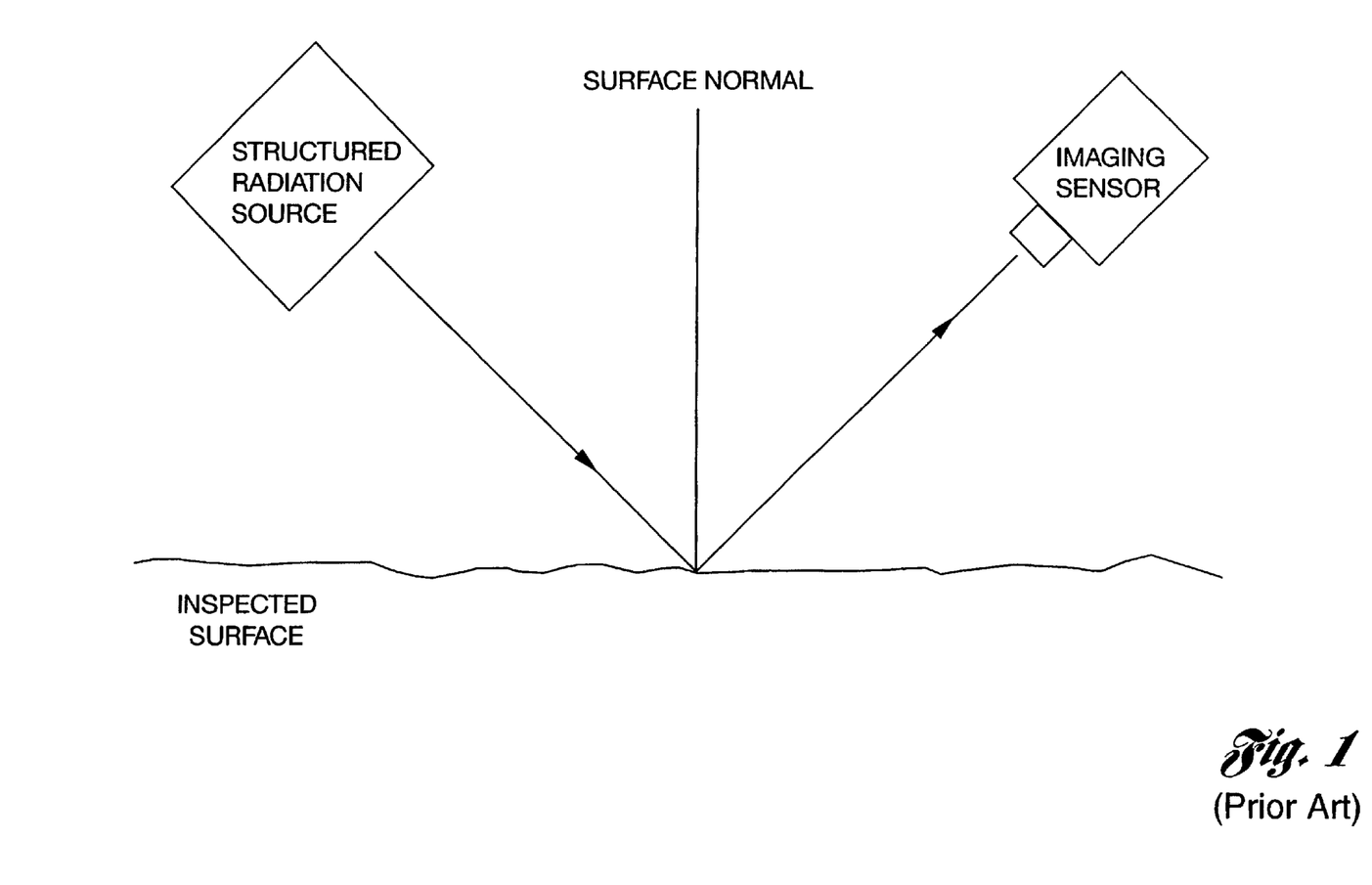
FIG. 1 is a schematic diagram of a prior art non-contact surface inspection system.

The non-contact inspection of a surface is often most easily accomplished by probing or illuminating the surface with light from a light source and sensing its reflected component as illustrated in FIG. 1. Deviations from surface flatness and other surface irregularities can be detected by noticing distortions and discontinuities in the reflected image. The light source typically has a known structure (so-called structured lighting).

This technique of probing a surface with a structured light source is extremely sensitive. An article by Lippincott and Stark entitled "Optical-Digital Detection of Dents and Scratches on Specular Metal Surfaces", Aug. 15, 1982, v. 21 (16), APPLIED OPTICS, describes a technique of imaging a series of regularly spaced lines through reflection from a specular surface. Apparatus embodying related ideas are described in U.S. Pat. Nos. 4,792,232; 5,436,726; and 5,237,404.

Automatic processing of images of structured lighting is desirable in an industrial setting. U.S. Pat. Nos. 4,792,232; 4,629,319; and 4,686,374 describe the electronic analog and digital processing of such images. Optical Fourier plane processing (or optical/digital processing) of images of structure lighting is also natural where the images contain periodic structures. U.S. Pat. No. 4,629,319 discloses a panel surface inspection system including an infrared (i.e. IR) source in the form of a $CO_2$ laser and an IR retro-reflective material to form an image on a pair of adjacent infrared detectors in a pyroelectric vidicon.

SUMMARY OF THE INVENTION

An object of the present invention is to provide a method and system for inspecting a low gloss surface of an object at a vision station utilizing a regular, extended pattern of radiation having a wavelength longer than the wavelength of visible light, but shorter than the dimensions of the surface defect.

Another object of the present invention is to provide a method and system for inspecting a low gloss surface of an object at a vision station utilizing infrared radiation such as broadband infrared radiation.

Yet, still another object of the present invention is to provide a method and system for inspecting a low gloss surface of an object at a vision station utilizing a regular, extended pattern of radiation having a wavelength longer than the wavelength of visible light, but shorter than the dimensions of the surface defect to automatically locate the surface defect.

Still another object of the present invention is to provide a relatively inexpensive method and system for inspecting a low gloss surface of an object at a vision station in a factory environment by using an extended source of structured infrared radiation.

Yet, still another object of the present invention is to provide a method and system for inspecting a low gloss surface of an object at a vision station to automatically locate a surface defect in the object utilizing a signal processing method which detects pattern distortions and correlates such pattern distortions between multiple images.

In carrying out the above objects and other objects of the present invention, a method is provided for inspecting a low gloss surface of an object at a vision station to automatically locate a surface defect in the object. The method includes the step of directing a regular, extended pattern of radiation, having a wavelength longer than the wavelength of visible light, but shorter than the dimensions of the surface defect, at the low gloss surface of the object to generate a corresponding reflected radiation signal. The method also includes the step of imaging the reflected light signal at the vision station to generate a first set of electrical signals representing the surface defect to be located. The method finally includes the step of processing the first set of electrical signals to obtain a second set of electrical signals representing pattern distortions in the reflected radiation signal caused by the surface defect to locate the surface defect in the object.

Further in carrying out the above objects and other objects of the present invention, a system is provided for inspecting a low gloss surface of an object at a vision station to automatically locate a surface defect in the object. The system includes a structured radiation source located at the vision station for directing a regular, extended pattern of radiation, having a wavelength longer than the wavelength of visible light, but shorter than the dimensions of the surface defect, at the low gloss surface of the object to generate a corresponding reflected radiation signal. The system also includes an imaging detector having an image plane located at the vision station for imaging the reflected radiation signal and to generate a first set of electrical signals representing the surface defect to be located. The system finally includes a signal processor coupled to the imaging detector for processing the first set of electrical signals to obtain a second set of electrical signals representing pattern distortions in the reflected radiation signal caused by the surface defect to locate the surface defect in the object.

Preferably, the radiation is infrared radiation, the source is an infrared source, and the imaging detector is an infrared camera.

Still further in carrying out the above objects and other objects of the present invention, a method is provided for inspecting a low gloss surface of an object located at a vision station. The method includes the step of directing a regular, extended pattern of radiation, having a wavelength longer than the wavelength of visible light, but shorter than the dimensions of the surface defect, at the low gloss surface of the object to generate a corresponding reflected radiation signal. The method also includes the step of converting the reflected radiation signal into a visible image for visual observation of pattern distortions in the reflected radiation signal caused by the surface defect.

Yet, still further in carrying out the above objects and other objects of the present invention, a system is provided for inspecting a low gloss surface of an object located at a vision station. The system includes a structured radiation source located at the vision station for directing a regular, extended pattern of radiation, having a wavelength longer than the wavelength of visible light, but shorter than the dimensions of the surface defect, at the low gloss surface of the object to generate a corresponding reflected radiation signal. The system also includes an image converter located at the vision station for converting the reflected radiation signal into a visible image for visual observation of pattern distortions in the reflected radiation signal caused by the surface defect.

Preferably, the radiation is infrared radiation, the source is an infrared source and the converter is an infrared image converter.

The improved method and system described herein use structured electromagnetic radiation having a longer wavelength than visible light to probe or inspect a surface. The radiation reflected from the surface being inspected is imaged by means of a sensor capable of responding to this wavelength. Since a surface appears glossy when the characteristic wavelength of its surface roughness is much shorter than that of the probing radiation, increasing the wavelength of probing radiation has the effect of making a diffusing surface more glossy. Thus, the technique of detecting surface irregularities or defects by noticing distortions and discontinuities in the reflected image of a light source having a known structure can be applied to surfaces which appear gloss-less to the naked eye.

The present invention is an improvement over current inspection methods for finding dings and dents (i.e. defects) on non-glossy surfaces in several ways:

1. The present invention preferably employs structured far infrared radiation. Previous methods have employed structured visible radiation: e.g. U.S. Pat. Nos. 5,436,726 and 4,792,232; or a point source of infrared radiation: e.g. U.S. Pat. No. 4,920,385 (which uses retroreflection); but no method to date has successfully utilized a structured infrared source.

2. The invention preferably uses broadband infrared radiation. Narrowband infrared radiation (such as that produced by a $CO_2$ laser or a single solid-state device contemplated by U.S. Pat. No. 4,629,319) is subject to speckling problems. Broadband radiation produced, for example, by heat tape radiating at 80° C., is not subject to speckling. The utilization of broad-band far infrared radiation in this invention is also advantageous in that large, extended infrared sources are simple and inexpensive to manufacture without special lenses and materials.

3. Since the optics of the infrared camera of the present invention are preferably focused on the surface being inspected, not the radiation source, and since the radiation source itself is comprised of infrared emitters with a significant spatial extent, unlike a laser source, the intensity of the radiation source appears to vary smoothly across its surface. There are not sharply defined "lines" of high-intensity radiation in the source. Rather, the high-intensity radiation maxima tend to blend smoothly into the low-intensity minima to produce periodic smooth fluctuation in imaged intensity. The advantage of this technique over techniques which involve the production and imaging of sharp lines is that defects can be identified not just as they fall on and distort a fine, intense line, but defects can be identified as they distort the light pattern between intensity maxima as well. U.S. Pat. No. 5,436,726 uses a related idea with visible light.

Previous attempts to extract defect information from an image of reflected structured light have depended upon using electronic or digital means of finding the location of particular edges or lines in an image and using the information thereby gathered about, for example, the inter-line spacing (U.S. Pat. No. 4,629,319 and Lippincott/Stark) or the least squares deviation of the line from its expected polynomial course (U.S. Pat. No. 4,792,232) to detect the presence or absence of surface defects. These methods suffer from being unable to detect defects which occur between lines, and from noise sensitivity. Moreover, except for infrared laser line projection methods (which themselves suffer from speckle problems), the current state of infrared optics and sensors is not sufficiently advanced to produce an inexpensive camera able to achieve a depth of field and resolution sufficient to simultaneously focus on both a light source and a surface when the source is more than 25 cm from the inspected surface (as is typically required in an industrial application). Thus, the method and system of the present invention, which is able to extract defect. information from an image of refleted structured radiation without needing to calculate edge locations or otherwise deduce a description of a "line", represent a significant advance.

The above objects and other objects, features, and advantages of the present invention are readily apparent from the following detailed description of the best mode for carrying out the invention when taken in connection with the accompanying drawings.

BEST MODE FOR CARRYING OUT THE INVENTION

Figure 2:
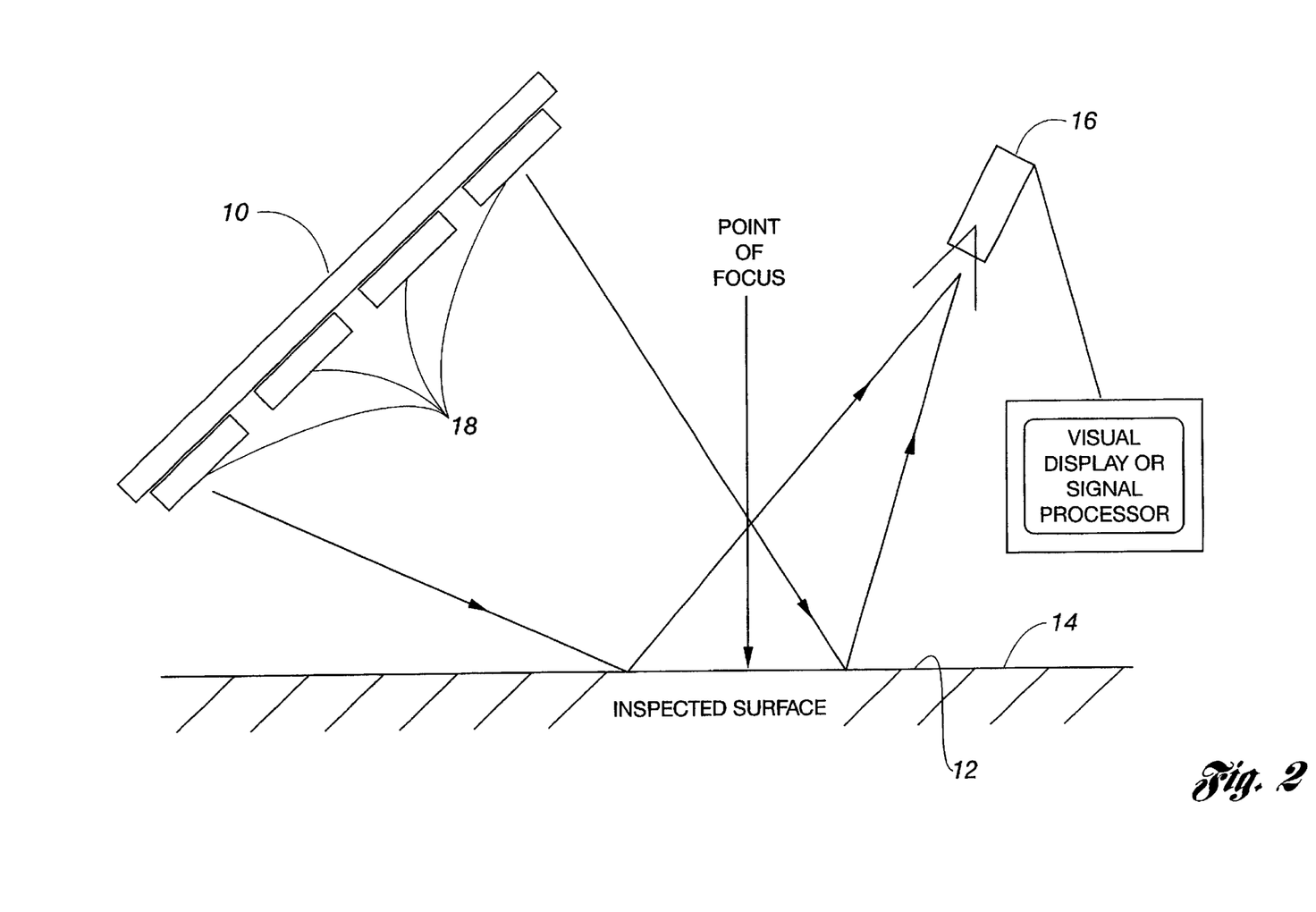
FIG. 2 is a schematic diagram illustrating the method and system of the present invention for inspecting a low gloss surface of an object at a vision station.

Referring now to FIG. 2, there is generally illustrated a method and system for inspecting a low gloss surface of an object at a vision station. In general, the system includes a structured radiation source, generally indicated at 10, located at the vision station for directing a regular, extended pattern of radiation, having a wavelength longer than the wavelength of visible light, but shorter than the dimensions of a surface defect at a low gloss surface 12 of an object 14 to be inspected to generate a corresponding reflected radiation signal. The system also includes at least one image converter or a camera 16. The image converter converts the reflected radiation signal into a visible image for visual observation of pattern distortions in the reflected radiation signal caused by the surface defect. The reflected radiation signal may be converted into a visible image on a fluorescent screen (i.e. visual display) of an image converter tube of the converter. Typically, a high aperture lens (not shown) forms an image of distant objects on a photocathode of an image tube sensitive to the radiation used and the visible final image is viewed through a magnifier.

As illustrated in FIG. 2, the camera 16 is coupled to a signal processor including a programmed computer system for processing the electrical signals generated by the camera 16 to automatically locate a surface defect in the object.

Preferably, the source 10 is a source of infrared radiation and the camera 16 is an area-scan infrared camera capable of responding to infrared radiation of the appropriate wavelength. Diverging infrared radiation is emitted from the source 10. This radiation reflects from the surface 12 to be inspected and is imaged by the infrared camera 16 after passing through optics (not shown) focused at or near the inspected surface.

Figure 3:
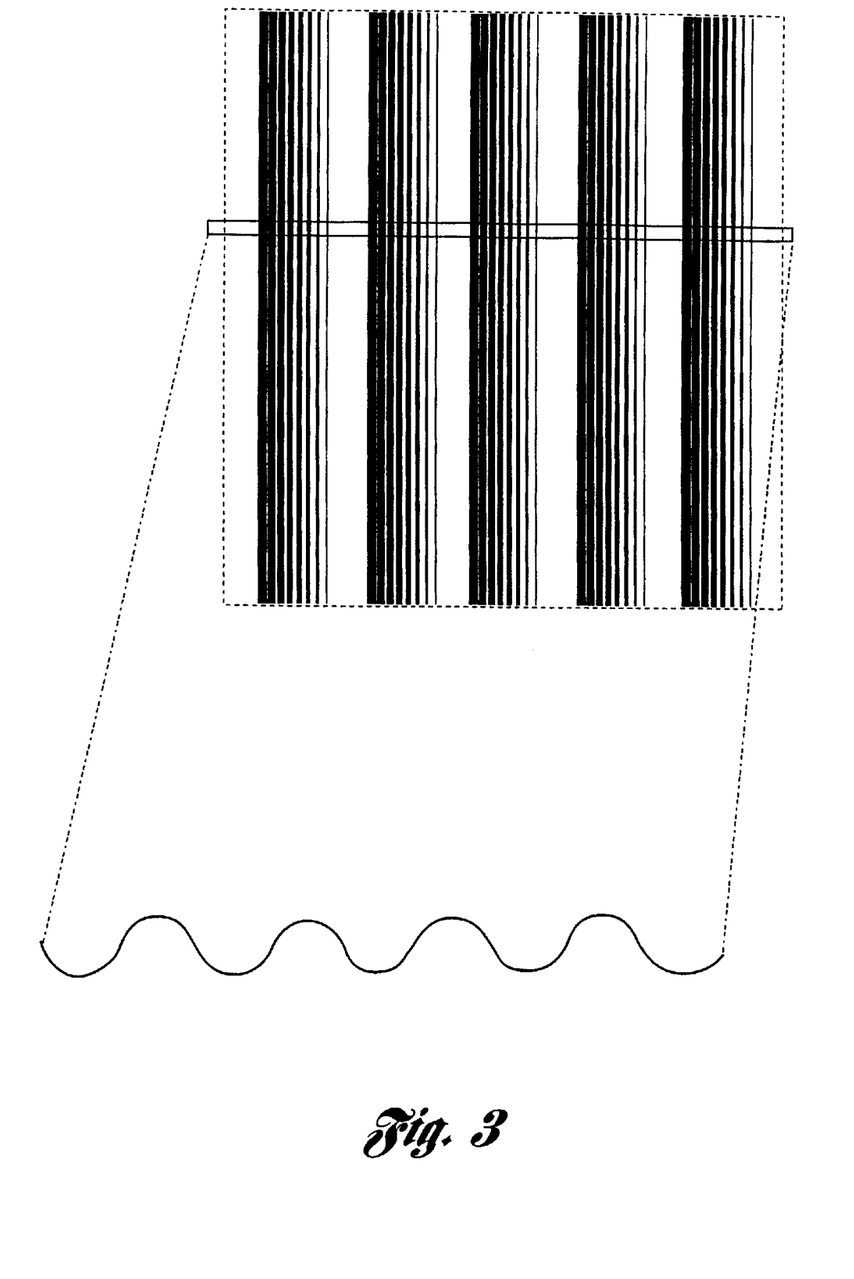
FIG. 3 illustrates the face of an infrared source having a spatial radiation pattern imposed thereon and the intensity profile of a horizontal line.

The face of the source 10 emitting toward the inspected surface 12 typically has a spatial radiation pattern imposed upon it as illustrated in FIG. 3 wherein a blurred image of the source 10 can be seen. Surface irregularities such as pits, dings, dents, out-dings, and bends distort the spatial pattern through reflection from the inspected surface 12. The distorted radiation pattern impinging upon the camera 16 typically is either converted to a visual display for human interpretation or the distorted radiation is converted to an analog electrical waveform or to a digital stream for signal processing including computer interpretation.

The possible wavelengths of the infrared source 10 and the detector camera 16 must be long enough so that the wavelength of the probing radiation is long compared with the characteristic dimension of the inspected part's surface roughness. Longer wavelengths are suitable so long as the longer wavelengths are not commensurate with the dimension of the defects to be detected. For galvanized bare metal surfaces, wavelengths in the 3–5 micron range (for example, by using the Inframetrics InfraCAM fitted with Germanium optics) as well as the 8–12 micron range (for example, by using the Amber Sentinel camera fitted with Germanium optics) function well.

The radiation pattern of the infrared source 10 need not have any particular geometry as long as the geometry is stable and easily resolvable by the camera 16. Because deformation of a regular, repeated geometry is detectable by both man and machine, one can use a repeating, quasi-parallel line structure in the source 10. An approximately regular grid of linear or point sources, for example, would also work.

Figure 4:
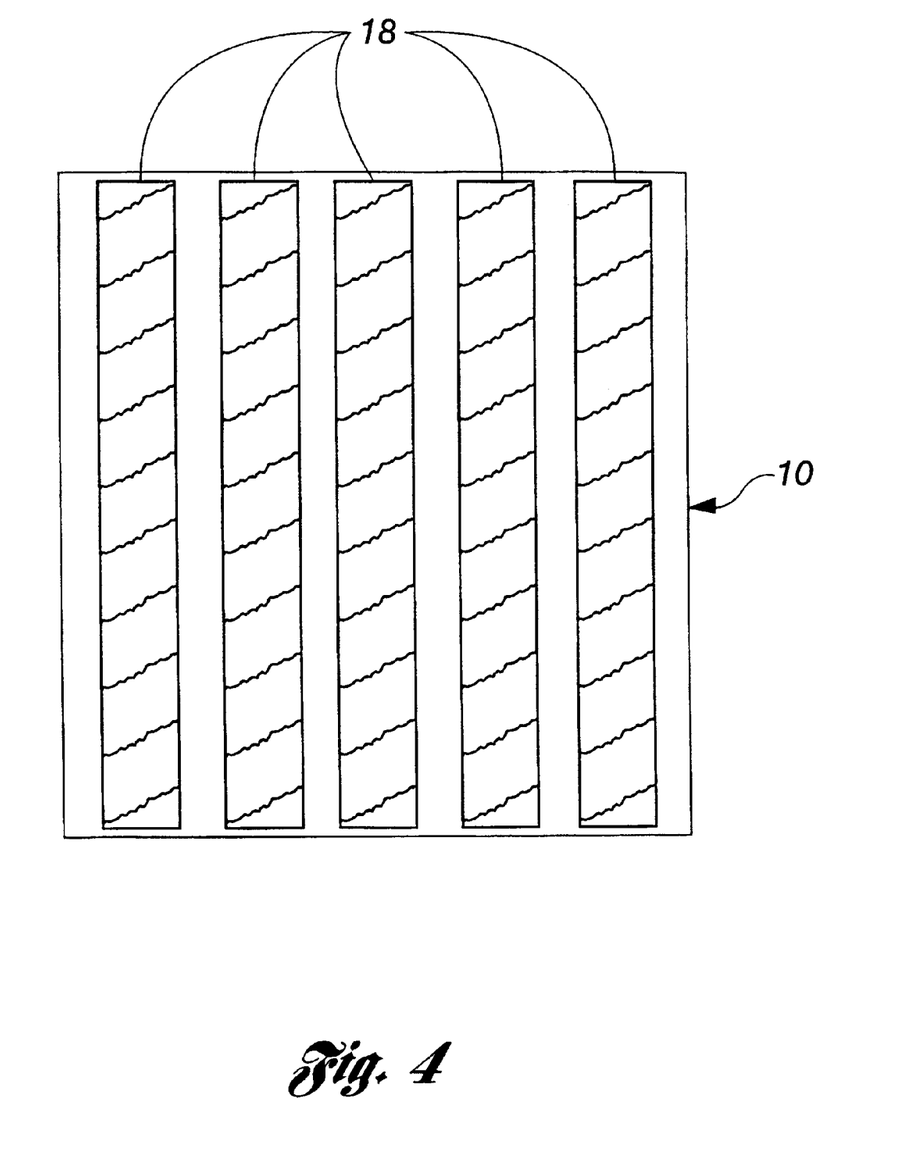
FIG. 4 is a diagram illustrating a preferred source of infrared energy in the form of resistance wires encased in a protective sheath defining strips of heat tape.

A preferred embodiment is to generate infrared radiation using resistance wires encased in strips 18 of a protective sheath such as fiberglass (i.e. such as multiple Duo-Tape heat tape by Amptek) electrically heated to approximately 80° C., as illustrated in FIG. 4. However, any source of infrared energy in the desired band is sufficient. Variations in the structure of the source 10 are produced by modifying the spacing, width, temperature, and number of the infrared emitters.

Infrared sources of smoothly varying intensity may be produced by the heat diffusion pattern on the front surface of plates of varying thicknesses and specific heats which are heated from behind by linear and/or point sources. An infrared source of smooth or stepped intensity gradations can also be produced by placing one or several infrared filters in front of a flat field infrared source.

Figure 5:
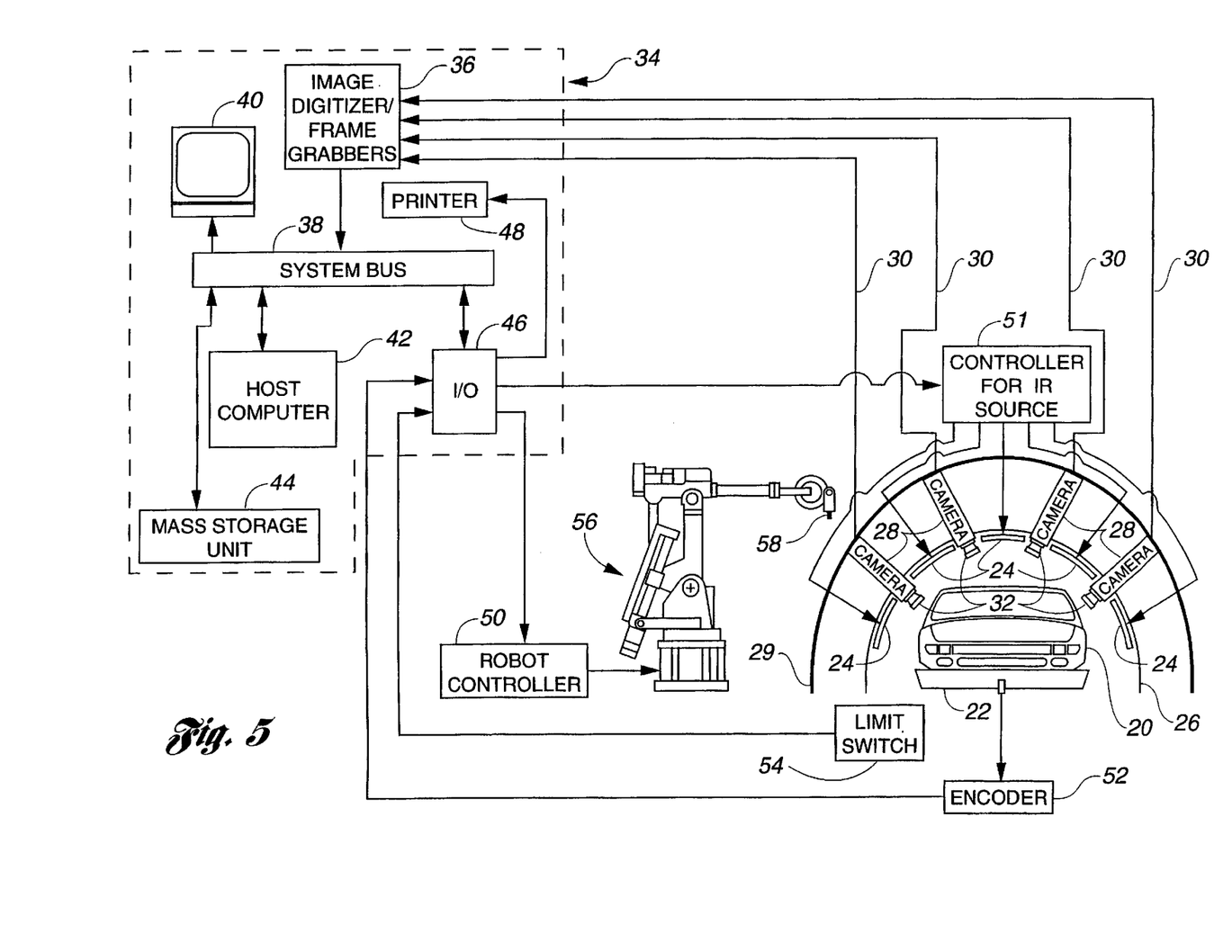
FIG. 5 is a schematic diagram of a system, for inspecting and marking multiple low gloss surfaces of an automotive assembly at a vision station to automatically locate a surface defect in the automotive assembly.

Referring now to FIG. 5, there is illustrated a method and system for inspecting a low gloss surface of an object such as an automotive assembly of bare metal parts at a vision station to automatically locate a surface defect in the assembly 20. The assembly 20 is mounted on a carriage 22 for movement, for example, on an assembly line through the vision station.

The structured radiation source of FIG. 5 preferably takes the form of strips of heat tape 24 secured, such as by double-backed tape, to pegboard arranged in the form of an arch 26 which completely surrounds the assembly 20 at the vision station. As in the case of the embodiment of FIG. 2, the heat tape 24 of the structured radiation source directs a regular, extended pattern of infrared radiation at the low gloss surfaces of the assembly 20 to generate corresponding reflected infrared radiation signals. The low gloss surfaces of the assembly 20 typically are bare metal (i.e. without any paint or oil applied thereto).

Imaging detectors typically in the form of infrared cameras 28 are also arranged in an arch 29 to image the reflected infrared radiation signals and generate a first set of electrical signals representing the surface defect to be located along lines 30 (i.e. cables). The infrared cameras 28 may be analogoic digital and preferably include a Geranium optical element or lens or suitable reflective optics 32 adapted to be focused at or near the low gloss surfaces of the assembly 20 for forming images containing surface defects in their image planes from the reflected infrared radiation signals. Each of the cameras 28 may be housed within a Pelco camera enclosure and power and RS-232 serial communications are fed by the cables 30 to the cameras 28 within their enclosures.

The signals on lines 30 from the cameras 28 are received by a signal processor, generally indicated at 34. When the signals from the cameras 28 are analog, the signal processor 34 typically includes image digitizer/frame grabbers 36. The image digitizer/frame grabbers 36 sample and digitize input signals from the cameras 28 and place each input image into a frame buffer having picture elements. Each of the picture elements may consist of a multi-bit number representing the brightness of that spot in the image. The cameras 28 may be digital to eliminate the need for the image digitizer/frame grabbers 36.

The image digitizer/frame grabbers 36 may be conventional frame grabber boards such as those manufactured by Matrox, Cognix, Data Translation, or other frame grabbers. Alternatively, the image digitizer/frame grabbers 36 may comprise vision processor boards such as made by Cognix. One or more of the above-noted boards may include one or more digital signal processors to process the digitized video signals.

A system bus 38 of the signal processor 34 may be either a PCI, an ECI, an ISA, or VL system bus or any other standard bus to allow inner system communication such as to a monitor 40.

A host computer 42 of the signal processor 34 may be a Pentium-based IBM compatible PC or other PC having a sufficient amount of RAM and hard disk space for performing the algorithms associated with the method and system of the present invention.

The signal processor 34 may be programmed at a mass storage unit 44 to include custom controls for image processing and image analysis as described hereinbelow.

The signal processor 34 also preferably includes input/output circuits 46 to allow the signal processor 34 to communicate with external devices such as a printer 48 to provide hard copy of an image if desired. The input/output circuits 46 also allow the signal processor 34 to communicate with a robot controller 50, the purpose of which will be described in greater detail hereinbelow. Finally, the input/output circuits 46 also allow the signal processor 34 to communicate with a controller 51 for the strips of heat tape 24 so that energization of the heat tape 24 can be programmably controlled for optimization purposes.

The input/output circuits 46 also allow the signal processor 34 to communicate with an encoder 52 which generates a position signal representative of position of the carriage 22 relative to the regular extended pattern of radiation generated by the heat tape 24. Preferably, the encoder is an optical incremental encoder mounted to a return wheel about which a chain drive of the assembly line moves. The system of the present invention knows when to look at the position signal provided by the encoder 52 through the use of a limit switch 54 which generates a signal input to the input/output circuits 46 of the signal processor 34 when the carriage 22 holding the assembly 20 reaches a predetermined position at the vision station.

Once the signal processor 34 locates a surface defect in the object, a signal is sent by the signal processor 34 via its input/output circuits 46 to the robot controller 50 which, in turn, generates a control signal based on location of the surface defect in the assembly 20. The control signal from the robot controller 50 is used by a surface marking mechanism in the form of a robot 56 which is movable between a withdrawn position, as illustrated in FIG. 5, and a surface marking position to mark the surface of the assembly 20 as a function of the location of the surface defect. For example, the robot 56 may have an end effector in the form of a marker 58 supported at the distal end of its arm to mark exactly where the defect occurs on the assembly 20.

The Processing Method

The method of the present invention relies upon the observation that a light pattern imaged multiple times in succession by reflection from a moving surface with a slowly varying topography will itself change only slowly. Indeed, although the surface may be moving, the light pattern projected upon it will appear to be nearly stationary. However, a topographical defect embedded on that surface such as a dent, ding, bend, etc., will appear, under the same circumstances as a distortion in the light pattern which travels at the speed of the moving surface.

Figure 6:
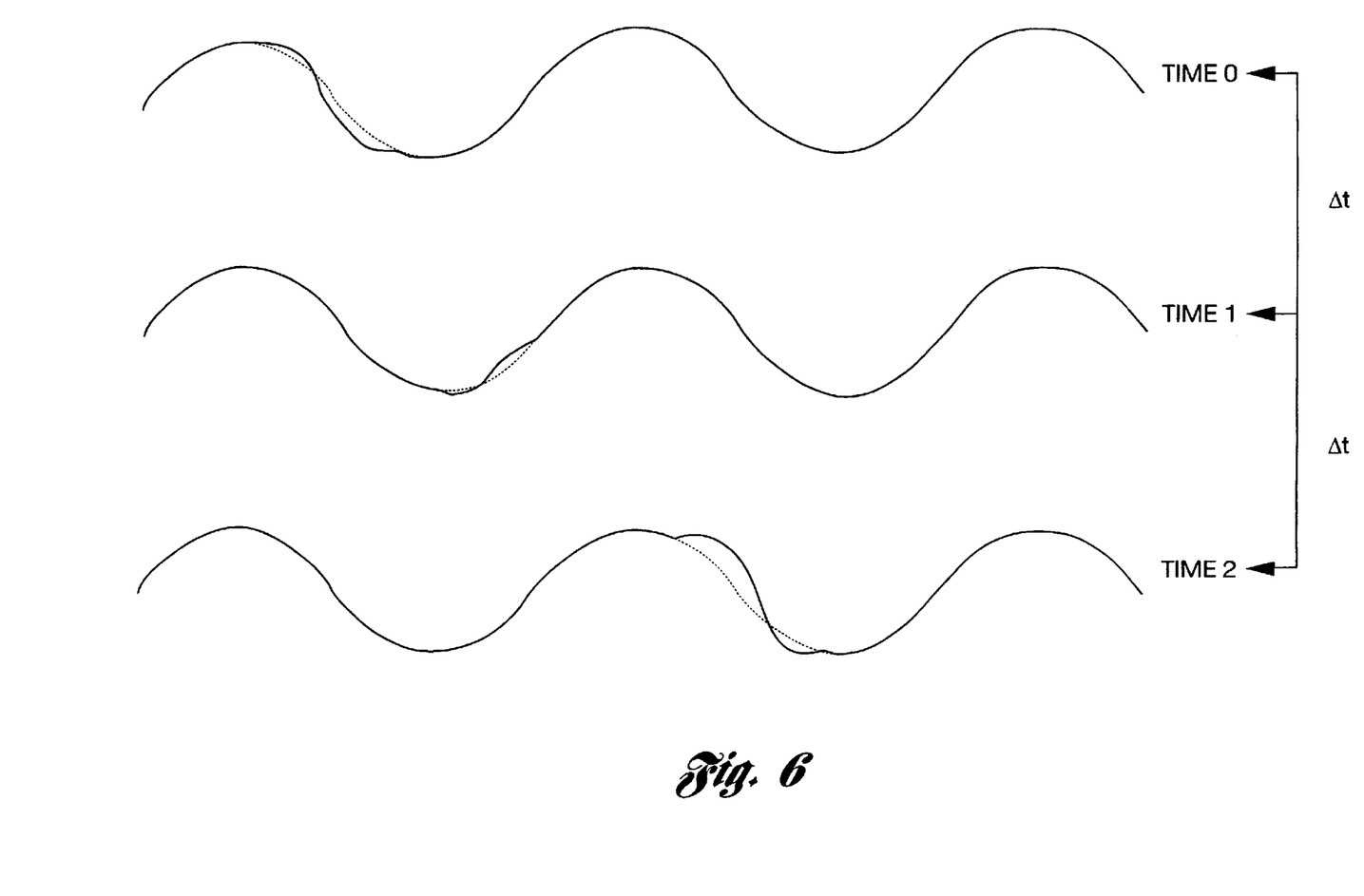
FIG. 6 is a graph of three electrical signals illustrating a traveling distortion caused by a defect.

The processing method or algorithm of the present invention which detects pattern distortions and correlates such pattern distortions between multiple images avoids the twin problems of noise sensitivity and the difficulty of detecting defects between "lines." FIG. 6 illustrates a traveling distortion such as may be caused by a topographic defect.

Figure 7:
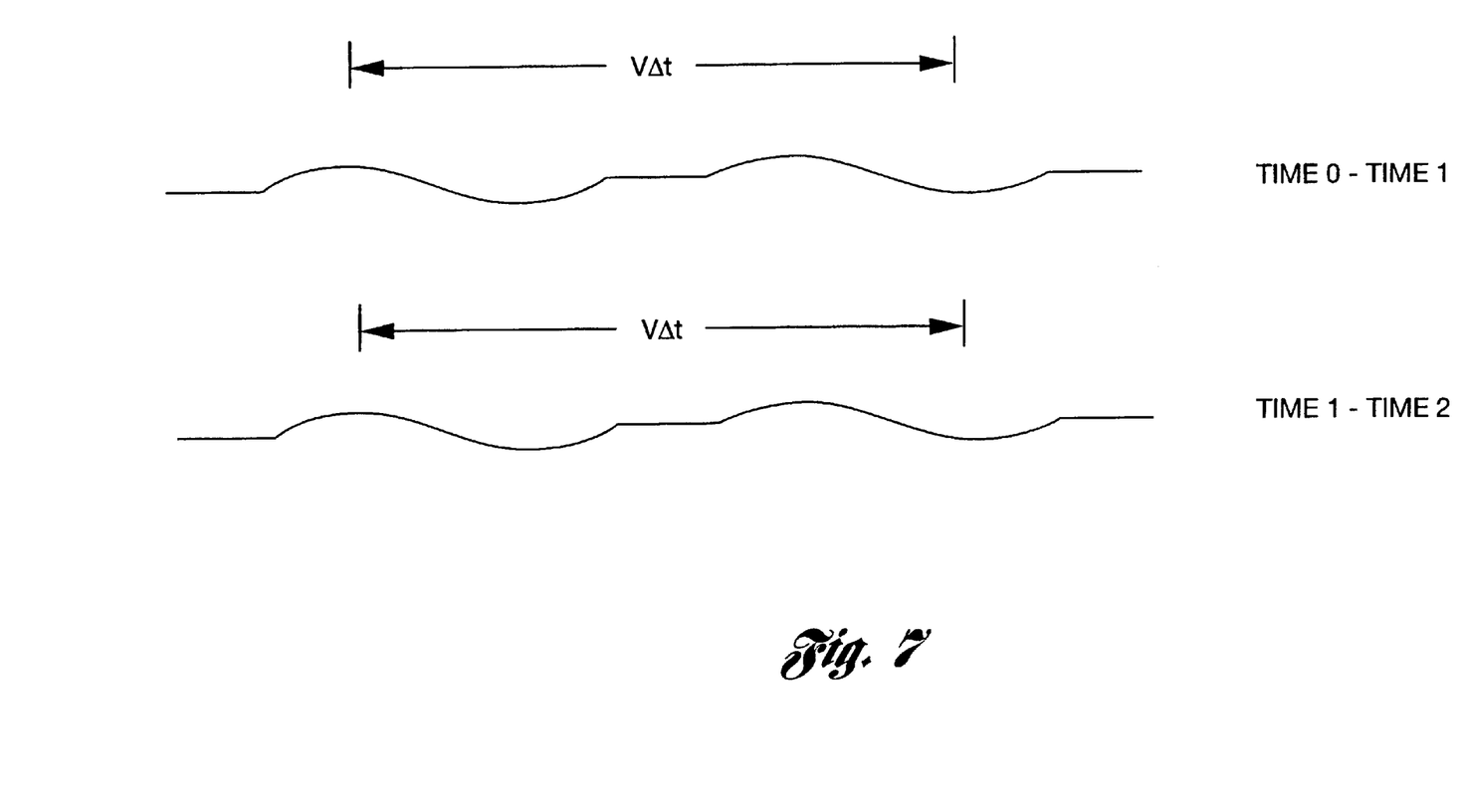
FIG. 7 illustrates a pair of subtracted images showing correlations at VAt for the waveforms of FIG. 6.

The steps of the processing method performed by the signal processor 34 are illustrated in FIG. 7. In a first step, an image is subtracted from its immediate predecessor. This yields a time-differential signal which enhances rapidly moving distortions such as are caused by topographic defects. This step is repeated as new images are acquired to provide a succession of subtracted images.

In the second step of the processing method, successive subtracted images are correlated to detect distortions traveling at the substrate speed. When the strength of correlation exceeds a predetermined threshold value, a defect is reported.

In an alternate embodiment, strong correlations within predetermined "masked" areas are not reported as defects. Such "masked" areas would correspond, for example, to known desirable features of an inspected surface such as seams, rivets, and punched holes.

Figure 8A:
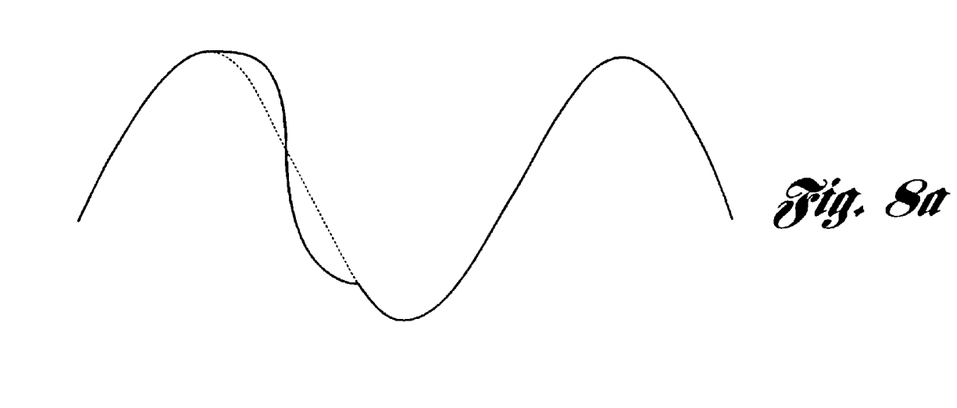
FIGS. 8a and 8b illustrates a pair of graphs which illustrate a classification of a defect as either an "out-ding" or an "in-ding", respectively.
Figure 8B:
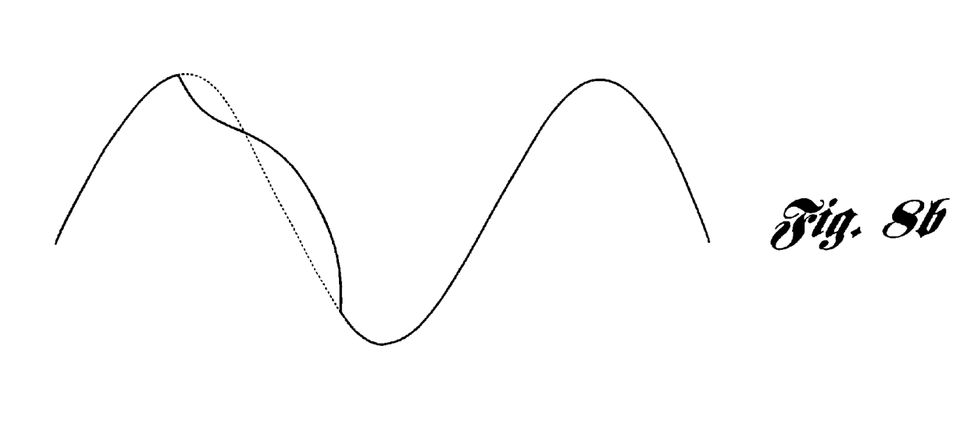

In an enhancement to this basic process, a defect is classified by the signal processor 34 according to whether it is an "out-ding" or an "in-ding" as illustrated by the graphs of FIGS. 8a and 8b, respectively. An "out-ding" (a raised defect on the inspected surface) tends to be brighter in the direction of local intensity maxima and darker in the direction of local minima. An "in-ding" (a depressed defect on the inspected surface) tends to be darker in the direction of local intensity maxima and lighter in the direction of local minima.

The method and system of the present invention can store (i.e. on the computer hard drive) and display (i.e. on the remote monitor 40) a sequence of visible images so that visual observation may occur at a different time-rate than the radiation signals are generated and received. Typically, each frame of video is associated with a line position shown by the output of the encoder 52. It is desirable to record a quick sequence of images and play them back for human evaluation more slowly, especially as the assembly 20 passes by the monitor 40.

While the best mode for carrying out the invention has been described in detail, those familiar with the art to which this invention relates will recognize various alternative designs and embodiments for practicing the invention as defined by the following claims.

What is claimed is:

1. A method for inspecting a low gloss surface of an object at a vision station to automatically locate a surface defect in the object, the method comprising the steps of:
   directing a regular, extended pattern of radiation, having a wavelength longer than the wavelength of visible light, but shorter than the dimensions of the surface defect, at the low gloss surface of the object to generate a corresponding reflected radiation signal;
   imaging the reflected light signal at the vision station to generate a first set of electrical signals representing the surface defect to be located; and
   processing the first set of electrical signals to obtain a second set of electrical signals representing pattern distortions in the reflected radiation signal caused by the surface defect to locate the surface defect in the object.

2. The method as claimed in claim 1 wherein the radiation is infrared radiation.

3. The method as claimed in claim 2 wherein the radiation is broadband infrared radiation.

4. The method as claimed in claim 1 further comprising the step of processing the second set of electrical signals to classify the surface defect in the object.

5. The method as claimed in claim 1 further comprising the steps of moving the object relative to the pattern of radiation at the vision station and generating a position signal representative of position of the object relative to the pattern of radiation at the vision station and wherein the first set of electrical signals are processed with the position signal to locate the surface defect in the object.

6. The method as claimed in claim 1 further comprising the step of generating a control signal based on location of the surface defect in the object and controllably moving a surface marking mechanism between a withdrawn position and a surface marking position in response to the control signal to mark the surface of the object as a function of the location of the surface defect.

7. The method of claim 1 wherein the step of processing includes the step of processing the second set of electrical signals together to correlate the pattern distortions.

8. A system for inspecting a low gloss surface of an object at a vision station to automatically locate a surface defect in the object, the system comprising:

a structured radiation source located at the vision station for directing a regular, extended pattern of radiation, having a wavelength longer than the wavelength of visible light, but shorter than the dimensions of the surface defect, at the low gloss surface of the object to generate a corresponding reflected radiation signal;

an imaging detector having an image plane located at the vision station for imaging the reflected radiation signal and to generate a first set of electrical signals representing the surface defect to be located; and a signal processor coupled to the imaging detector for processing the first set of electrical signals to obtain a second set of electrical signals representing pattern distortions in the reflected radiation signal caused by the surface defect to locate the surface defect in the object.

9. The system as claimed in claim 8 wherein the radiation is infrared radiation, the structured radiation source is an infrared radiation source and the imaging detector is an infrared imaging detector.

10. The system as claimed in claim 9 wherein the infrared imaging detector is an infrared camera.

11. The system as claimed in claim 8 further comprising an optical element adapted to be focused at or near the low gloss surface for forming an image containing the surface defect in the image plane from the reflected radiation signal.

12. The system as claimed in claim 8 wherein the regular, extended pattern of radiation has a parallel line structure.

13. The system as claimed in claim 8 wherein the structured radiation source includes a plurality of electrically-heated resistive wires.

14. The system as claimed in claim 8 wherein the structured radiation source includes a plurality of strips of electrically-heated heat tape.

15. The system as claimed in claim 8 further comprising means for moving the object relative to the pattern of radiation at the vision station and a sensor coupled to the means for moving and the signal processor to generate a position signal representative of position of the object relative to the pattern of radiation at the vision station and wherein the first set of electrical signals are processed with the position signal by the signal processor to locate the surface defect in the object.

16. The system as claimed in claim 8 further comprising a controller coupled to the signal processor for generating a control signal based on location of the surface defect in the object and a surface marking mechanism movable between a withdrawn position and a surface marking position in response to the control signal to mark the surface of the object as a function of the location of the surface defect.

17. The system as claimed in claim 16 wherein the mechanism includes a robot and wherein the controller is a robot controller.

18. The system as claimed in claim 8 wherein the signal processor processes the second set of electrical signals to classify the surface defect in the object.

19. The system as claimed in claim 8 wherein the structured radiation source directs the pattern of radiation at a plurality of low gloss surfaces of the object to generate a plurality of corresponding reflected radiation signals and wherein the system further comprises a plurality of imaging detectors located at the vision station for imaging the plurality of reflected radiation signals.

20. The system of claim 8 wherein the signal processor processes the second set of electrical signals together to correlate the pattern distortions.

21. A method for inspecting a low gloss surface of an object located at a vision station, the method comprising the steps of:

(a) directing a regular, extended pattern of radiation, having a wavelength longer than the wavelength of visible light, but shorter than the dimensions of the surface defect, at the low gloss surface of the object to generate a corresponding reflected radiation signal; and (b) converting the reflected radiation signal into a visible image for visual observation of pattern distortions in the reflected radiation signal caused by the surface defect.

22. The method of claim 21 wherein the radiation is infrared radiation.

23. The method of claim 21 wherein steps (a) and (b) are repeated to obtain a sequence of visible images and wherein the method further comprises the steps of storing the sequence of visible images and displaying the stored sequence of visible images so that visual observation may occur at a different time-rate than the reflected radiation signals are generated.

24. A system for inspecting a low gloss surface of an object located at a vision station, the system comprising:

a structured radiation source located at the vision station for directing a regular, extended pattern of radiation, having a wavelength longer than the wavelength of visible light, but shorter than the dimensions of the surface defect, at the low gloss surface of the object to generate a corresponding reflected radiation signal; and an image converter located at the vision station for converting the reflected radiation signal into a visible image for visual observation of pattern distortions in the reflected radiation signal caused by the surface defect.

25. The system of claim 24 wherein the radiation is infrared radiation, the source is an infrared radiation source and the image converter is an infrared image converter.

26. The system of claim 24 further comprising a storage device coupled to the image converter for storing a sequence of visual images and a display coupled to the storage device for displaying the stored sequence of visible images so that visual observation may occur at a different time-rate than reflected radiation signals are generated.

* * * * *